Figure 1:
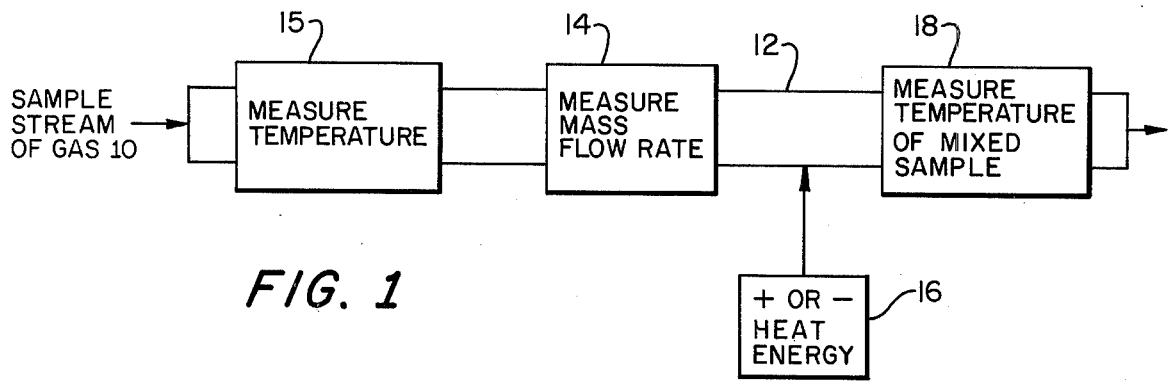

United States Patent [19]

Gardiner

[11] 4,028,942

[45] June 14, 1977

[54] HYGROMETER

[76] Inventor: Frank J. Gardiner, 3 Ledge Road, Cumberland Foreside, Maine 04110

[22] Filed: Jan. 19, 1976

[21] Appl. No.: 650,115

[52] U.S. Cl. .................................. 73/335; 73/29
[51] Int. Cl.² ...................................... G01N 25/56
[58] Field of Search .......... 73/335, 61.1 R, 194 M, 73/29

[56] References Cited

UNITED STATES PATENTS

| | | | |
|---|---|---|---|
| 3,216,257 | 11/1965 | Ford | 73/335 |
| 3,265,301 | 8/1966 | Amdur et al. | 73/29 X |
| 3,532,270 | 10/1970 | Schoen, Jr. | 73/29 X |
| 3,661,724 | 5/1972 | Strickler | 73/335 X |
| 3,898,882 | 8/1975 | Prokopius | 73/194 M |

*Primary Examiner*—Richard C. Queisser
*Assistant Examiner*—Joseph W. Roskos
*Attorney, Agent, or Firm*—Schiller & Pandiscio

[57] ABSTRACT

A sensing device is used to measure absolute humidity of a sample stream of gas by measuring the mass flow rate of the sample, adding or subtracting a known amount of heat energy (per unit mass of the sample stream) to the heat energy of the sample and measuring the temperature of the sample before and after the heat energy of the sample is changed. These measured parameters are then used to calculate the specific heat of the sample, which in turn can be used to calculate the water vapor content of the gas.

21 Claims, 2 Drawing Figures

U.S. Patent

June 14, 1977

4,028,942

HYGROMETER

This invention relates to the measurement of humidity and more particularly to a device and method of measuring the absolute humidity in a gas flow stream.

The present invention has particular application to industrial drying processes in which heated air is blown over or through a material or product to be dried. Such processes are very common in the manufacture of paper and textiles as well as plastics and many other industrial materials. Typically, the air used for drying the product is heated between temperatures of 50° C and 600° C, and is passed over or through the product and then discharged. To conserve energy, it is desirable to recirculate and reheat this hot air and to pass it through the product many times before discharging it, so that the heat energy in the air will be used as efficiently as possible. However, each time the air recirculates through the wet product, the absolute humidity (defined as the number of grams of water vapor contained in one gram of dry air) increases until it is no longer economically feasible to continue recirculation. It therefore, has become desirable to provide a humidity sensing device, also known as a hygrometer, for measuring the absolute humidity of the recirculating air so that some or all of it may be discharged when the absolute humidity exceeds some predetermined value.

Many of the commercially available hygrometers which are adapted to be used in heating and air-conditioning systems are designed for much lower temperature and humidity ranges than the temperature and humidity ranges encountered in the above-described industrial processes. One known type of humidity sensor operates on a change in some physical or chemical characteristic in the sensor with a change in humidity. For example, certain aqueous crystals, such as lithium chloride, will change their electrical properties with changes in humidity. However, such crystals operate in temperature ranges which do not exceed approximately from 100° C to 150° C. Another type of known hygrometer depends on the distortion of a plastic or animal fiber (such as hair) but the operation of such sensors are again limited by operating temperatures which are even less than 120° C.

Other sensors require the humid gas to be sampled, cooled and brought into a test chamber where the humidity is measured under desirable conditions. Sensors of this type often determine the dew point of the humid gas by chilling the gas near a light reflective element such as a mirror. As the water vapor condenses on the mirror at the dew point, the reflectivity of the mirror changes and the temperature at the dew point can thus be determined. These latter sensors are not however, desirable for industrial processes of the type described where the hot gas used for drying usually contains more water than saturated air at near ambient temperatures. Thus, sampling and cooling a gas of high absolute humidity (wherein the gas may have an absolute humidity of up to 0.7), may result in a loss of humidity of the samples gas as a result of condensation. Further, the problems in pumping the gas from the process stream into a sampling chamber also makes this approach undesirable.

Many of these hygrometers and others not mentioned are particularly unsatisfactory in large and fast operations, such as paper making. For example, a typical paper-making machine produces about 1,500 linear meters of 4 meter wide paper/min. This paper is usually passed over an air dryer for about 0.5 seconds to dry. Few of the known hygrometers will respond so quickly to changes in humidity nor can they operate efficiently for any substantial length of time in dusty and dirty atmospheres, such as those encountered in paper and textile drying.

Generally, therefore, it is the principle object of the present invention to overcome the above noted problems of the prior art.

The present invention makes use of the principle that there is a relationship between the absolute humidity and the specific heat of the gas stream whose water vapor content is being measured. More specifically, it is generally known that the specific heat of water vapor is about 1.9 (joules/gm° C) and the specific heat of dry air (with no water vapor present) is about 1.0 joules/gm° C. Thus, the specific heat of dry air is about ½ that of water vapor. Further, in processes where internal combustion is occurring, certain other gases may be present or absent in the gas stream in varying amounts. These gases generally have a specific heat approximating the specific heat of dry air. For example, $CO_2$, nitrogen and oxygen have specific heats of 0.83, 1.04, and 0.91 (joules/gm° C), respectively. Thus, the specific heat of a gas stream with or without these gases will be approximately the same. By measuring the specific heat of a gas stream, the water vapor content of the stream can be readily and uniquely deduced. The relationship of specific heat of the gas stream and the absolute humidity of that stream is related by the following equations:

$$c_m = c_A + \gamma c_{wv}; \tag{1}$$

or $$\gamma = \frac{c_m - c_A}{c_{wv}} \tag{1a}$$

Where
 $\gamma$ = the absolute humidity defined by the weight of the vapor in a gas sample divided by the weight of the dried air of that sample (dimensionless);
 $c_m$ = the specific heat at constant pressure of the gas stream (joules/gm° C);
 $c_A$ = the specific heat of dry air of zero absolute humidity at constant pressure (joules/gm° C); and
 $c_{wv}$ = the specific heat of water vapor at constant pressure (joules/gm° C).

The present invention further makes use of certain principles of thermodynamics, wherein the specific heat of a gas can be calculated by adding or subtracting a known amount of heat energy to the heat energy of the gas of known mass and then measuring the change in temperature of the resulting mixture from that of the original gas. More specifically, the following equation illustrates this thermodynamic principle.

$$M_m [c_m] [T_{out} - T_{in}] = \Delta Q; \tag{2}$$

or $$c_m = \Delta Q / M_m [T_{out} - T_{in}] \tag{2a}$$

Wherein
 $M_m$ = the mass flow rate of the resulting gas mixture per unit time (grams/sec.);
 $T_{out}$ = the temperature of the resulting mixture (° C);

$T_{in}$ = the measured temperature of the gas sample before the heat energy is added or subtracted (° C); and $\Delta Q$ = the amount of energy added or subtracted to the sample stream of gas per unit time (watts).

Substituting equation (2a) into (1a) the absolute humidity can be calculated as follows:

$$\gamma = \frac{\Delta Q}{C_{wv} M_m [T_{out} - T_{in}]} - \frac{C_A}{C_{wv}} \quad (3)$$

It is therefore a specific object of the present invention to provide a device for and method of measuring the specific heat of a gas stream in order to measure the absolute humidity of the stream.

Another object of the present invention is to provide a device for and method of determining the specific heat of a sample stream of gas by adding or subtracting a predetermined amount of heat energy and measuring the change in temperature between the original gas and the resulting mixture.

And another object of the present invention is to provide a hygrometer for and method of determining the water vapor content of a gas stream at relatively high temperatures and with relatively high absolute humidities quickly and accurately, regardless of the particulate content of the stream.

These and other objects of the present invention are achieved by passing at least a portion of the gas stream through a sensing device, so that the mass flow rate can be measured. The heat energy content of the sampled portion is changed by a known amount (per unit mass of the sampled portion) and the temperature of the sampled portion of the gas is measured both before and after the heat energy content change. The measured parameters then enable the absolute humidity to be determined by reason of equation (3) above.

Other objects of the present invention will in part be obvious and will in part appear hereinafter. The invention accordingly comprises the processes involving the several steps and the relation and order of one or more steps with respect to each of the others; and the apparatus possessing the construction, combination of elements, and the arrangement of parts which are exemplified in the following detailed disclosure, and the scope of the application of which is indicated in the claims.

Figure 2:
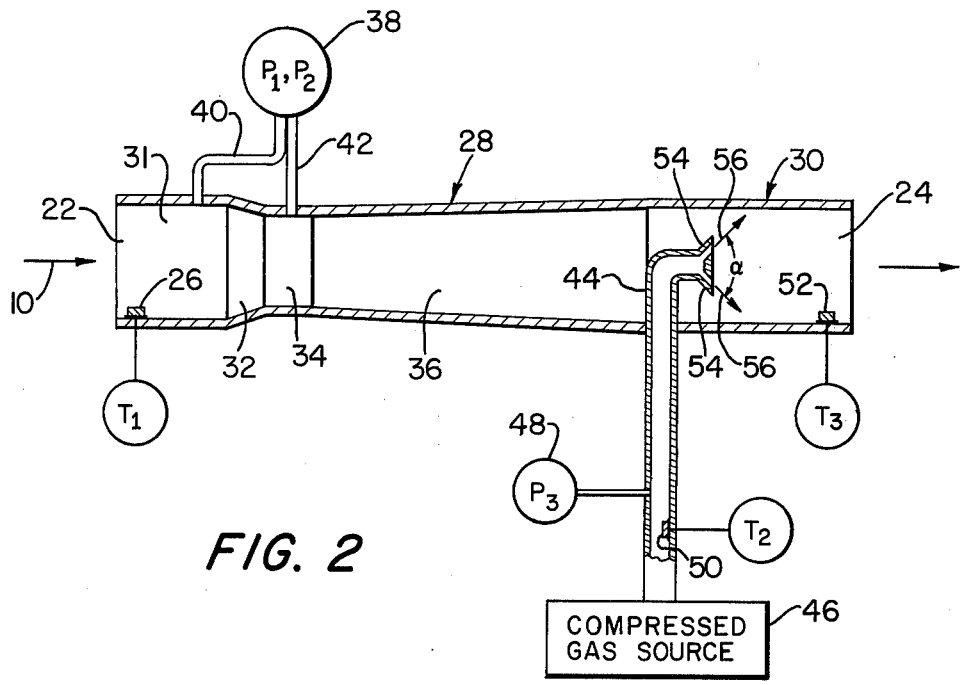

For a fuller understanding of the nature and objects of the present invention, reference should be had to the following detailed description taken in connection with the accompanying drawing wherein:

FIG. 1 shows schematically apparatus embodying the principles of the present invention; and FIG. 2 shows a preferred embodiment of the present invention.

Referring to FIG. 1, a gas stream 10 which is to be tested is passed at least in part through conduit 12. The latter may be a portion of a pipe or stack carrying the gas stream or it may be a hollow tubular element or the like, inserted inside a pipe or duct carrying the gas stream with the axis of elongation of the conduit oriented substantially parallel to the gas stream so that a sample portion of the latter can pass through the conduit substantially unimpeded. Means 14 are provided at the upstream end of conduit 12 for measuring the mass flow ($M_m$) of the stream passing therethrough. Means 15 are also provided at the upstream end of conduit 12 for measuring the temperature ($T_{in}$) of the sample stream passing through the conduit. It will be appreciated that when conduit 12 is placed in or joins a larger pipe or duct, means 15 may be positioned outside conduit 12 in the main stream of gas since the sample entering the conduit will be at the same temperature. Means 16 disposed downstream from means 14 and 15, are provided for summing a known amount of heat energy ($\Delta Q$) with the heat energy of the sample stream of gas in the conduit. This known amount of heat energy may either be a positive or a negative quantity. More specifically, where the known amount of heat energy is a positive quantity, heat energy per unit mass of the gas is added to the gas as it passes through the conduit. Conversely, however, means 16 may serve to cool the sample stream so that a known amount of heat energy per unit of mass of the gas is actually subtracted from the gas stream sample as it passes through the conduit.

Finally, means 18 is provided at the downstream end of the conduit for measuring the temperature ($T_{out}$) of the gas as it passes out of the conduit. By properly metering the parameters measured by means 14, 15, 16 and 18, the absolute humidity of the gas stream can readily be calculated in accordance with equation (3) above.

Referring to FIG. 2, a preferred embodiment of the present invention is described wherein the conduit of FIG. 1 is in the form of a hollow, substantially cylindrical elongated duct 20 the latter being adapted to be inserted in or pneumatically coupled to a larger duct (not shown) through which the main stream of gas 10 is flowing. Duct 20 is oriented so that a sample of the main gas stream can enter at inlet 22 and exit at outlet 24. Positioned adjacent inlet 22 is temperature sensing means 26, such as a thermistor (including platinum resistance thermometers), thermocouple or any similar known device for measuring the temperature of the stream of gas entering duct 20. The interior of duct 20 comprises Venturi tube 28 and mixing section 30 connected to tube 28 at the downstream end of the latter Venturi tube 28 and the temperature sensing means 26 constitute means for determining the mass flow rate of the portion of sample stream of gas 10 entering at the inlet 22. As well known in the art Venturi tube 28 comprises seriatim, elongated inlet section 31 with a constant cross-sectional diameter through its length, frustoconically tapered section 32 which decreases in cross-sectional diameter in the direction of the flow of the stream, throat or constricted section 34 with a constant cross-sectional diameter, and a diffuser or tapered exit cone section 36 which increases in cross-sectional diameter in the direction of the flow of the stream.

As well known in the art, the pressure of the sample stream in inlet section 31 will decrease from a pressure $P_1$ to a pressure $P_2$ as it passes from inlet 22 to throat 34 and is subsequently retarded or reduced by gradual deceleration to its original pressure $P_1$ (with a minimum of turbulence) as it passes through diffuser 34 into mixing section 30. Pressure measuring means, shown generally at 38, such as a manometer or any other device known in the art, is connected through lines 40 and 42 to inlet section 31 and throat 34 respectively, in order to measure the corresponding pressures $P_1$ and $P_2$. Lines 40 and 42 can be connected to the Venturi tube with a single pressure connection into the inlet section 31 and throat 34 respectively, or in the alternative as well known in the art the connection to each section 31 and throat 34 may include a plurality of openings radially spaced around the tube pneumatically connected to a common outlet to form a piezometer ring, the advantages of which are well known. Assuming the sample stream performs substantially as an ideal gas, measuring the pressure $P_1$ of sample stream 10 in inlet 22, and the pressure $P_2$ in throat 34, the mass flow rate, $M_1$, of the sample stream through tube 28 can be calculated from the following well known equation:

$$M_1 = \rho A_2 \, [P_2/P_1]^{1/k} \sqrt{\frac{[2gC_pT_1\,(1 - P_2/P_1)^{(k-1)/k}]}{[1 - (A_2/A_1)^2\,(P_2/P_1)^{2/k}]}} \qquad (4)$$

where $M =$ the mass flow rate of the stream portion passing through the Venturi tube 28;
$\rho =$ the density of sample stream 10;
$A_2 =$ the minimum cross-sectional area of throat 34;
$A_1 =$ the cross-sectional area of the inlet section 31;
$P_2 =$ the pressure of sample stream 10 measured at throat 34;
$P_1 =$ the pressure of sample stream 10 measured in inlet section 31;
$k =$ the ratio of $c_p/c_v$;
$c_p =$ the specific heat of the gas at constant pressure;
$c_v =$ the specific heat of the gas at constant volume;
$g =$ the gravity constant; and
$T_1 =$ the temperature of the gas stream portion measured by temperature measuring means 26 adjacent inlet 22.

In the embodiment shown, means are provided for adding or subtracting a known amount of heat energy to or from the sample stream of gas 10. Such means comprises fluid injector tube 44, which extends through the wall of mixing section 30 into the sample stream passing through duct 20. The injector tube is placed at the beginning of mixing section 30 and injects a fluid through a nozzle into the sample stream passing through the instrument in order to change the heat content of the sample stream by a measured amount. As will be more evident hereinafter, the fluid injected by injector tube 44 can be a liquid or a gas. Preferably, the fluid is air at room temperature derived from a standard compressed air system 46 which operates at a predetermined metered gauge pressure $P_3$. This pressure $P_3$ as well as the temperature $T_3$ of the compressed air are preferably measured by conventional instruments such as pressure gauge 48 and temperature sensing means 50. Injection tube 44 preferably includes a plurality of "critical" or sonic nozzles or jets 54 wherein the local air speed of the injected air is equal to the velocity of sound. This type of nozzle, which is well known in the art, has the advantage that the mass flow through the injection tube 44 is independent of the pressure, $P_3$, behind the nozzle as long as this pressure is less than that of the critical pressure. As well known in the art, assuming that the injected fluid performs as an ideal gas, the mass flow rate of the fluid out of the nozzle is defined by the following equation:

$$M_2 = P_3 A \sqrt{\frac{Kg}{RT_2} \left(\frac{2}{K+1}\right) \frac{K+1}{K-1}} \qquad (5)$$

wherein $M_2 =$ the mass flow rate of the fluid out of the nozzle;
$R =$ a constant defined by the difference between the specific heat of the gas at constant pressure and the specific heat of the gas at constant volume $(c_p - c_v)$;
$k =$ the ratio of specific heats of $c_p/c_v$;
$T_2 =$ the temperature of the gas measured by means 50;
$P_3 =$ the pressure measured by gauge 48; and
$A =$ the minimum cross-sectional area of the output nozzles 54 of the injector tube.

The injected fluid must be at a temperature which is substantially different from the temperature of the gas stream portion flowing through the Venturi tube 28, in order to effect as large as possible temperature change in the sample gas stream. For example, in industrial processes where the present invention is particularly useful, sample stream 10 is frequently at elevated temperatures such as 200° C. The injection of compressed shop air at room temperature effectively reduces the temperature of the sample stream even though the amount of shop air introduced may be small. For example, where the mass flow rate of shop air introduced into the sample stream is only 10% of the mass flow rate of the sample stream of gas 10, and the temperature difference between the shop air and the sample stream is about 200° C, the change in temperature effected by the injected air will be about 20° C.

Injector tube 44 and the mixing section 30 are designed so that good mixing is achieved as promptly as possible and so that by the time the mixed gas stream reaches outlet 24 of instrument 20 it is of a uniform temperature. The temperature of this mixed gas is measured at outlet 22 by temperature measuring means 52. Temperature sensing means 52 is typically the same as temperature sensing means 26 and 50, and therefore will not be described in detail.

Injector tube 44 can also serve to impart momentum to sample stream 10 entering the mixing section 30 from Venturi tube 28. Accordingly, the nozzles 54 are designed to inject the fluid so as to provide maximum mixing of the gas stream and injected fluid in the shortest distance possible as well as enhancing the momentum of the sample stream of gas 10. It will be appreciated that if nozzles 54 inject the fluid $M_2$ in a downstream direction the jets act as small pumps and thus assist in propelling the main gas through the instrument. In such a case the jets will impart momentum to stream 10, but will tend to form an undesirably unmixed core of gas $M_2$ near the center of the mixing section 30. Better mixing in a shorter distance will be achieved by pointing the jets upstream but this will result in negative momentum being imparted to the main gas stream 10 thus retarding the flow of the stream through the instrument. It is preferred therefore that nozzles 54 inject the fluid in a plurality of directions which define the surface of a cone (as indicated by arrows 56) having a conical angle $\alpha$ between 90° and 180° so that each stream is injected at an angle with respect to the flow of the sample stream between 45° and 90°.

By properly calculating the mass flow rates ($M_1$ and $M_2$) of the sample stream and the fluid flowing through Venturi tubes 28 and injector tube 44, respectively and measuring the temperatures ($T_1$, $T_2$ and $T_3$) by means 24, 48 and 52, the amount of water vapor present in the sample stream can easily be calculated. It will be evident that in view of equations 1-5 the equation for calculating the absolute humidity of a main gas as a function of $M_1$, $M_2$, $T_1$, $T_2$ and $T_3$ is as follows:

$$\gamma = \frac{(T_1 - T_2) - \left(1 + \frac{M_1}{M_2}\right)(T_1 - T_3)}{\left(\frac{C_{wv}M_1}{C_A M_2} + 1\right)(T_1 - T_3) - (T_1 - T_2)} \quad (6)$$

where
- $\gamma$ = the absolute humidity of the sample stream of gas 10;
- $T_1$ = the temperature measured by sensing means 26;
- $T_2$ = the temperature measured by temperature sensing means 50;
- $T_3$ = the temperature measured by means 52 of the mixed stream;
- $M_1$ = the mass flow calculated from equation (4) of the sample stream of gas 10 passing through Venturi tube 28;
- $M_2$ = the mass flow of the fluid injected by injector tube 44 calculated in accordance with equation (5);
- $c_{wv}$ = the specific heat of water vapor at constant pressure;
- $c_A$ = the specific heat of dry air at constant pressure.

As previously mentioned, although the fluid injected through injector tube 44 is described as preferably being compressed air, other types of fluids can be used to add or subtract heat energy to stream 10. For example, the fluid may be a liquid such as water. In such a case injector tube 44 is modified in a manner well known to those skilled in the art so as to atomize the water into small particles which will rapidly evaporate in stream 10 as it passes through mixing section 28. Since the latent heat of vaporization of water (approximately 2400 joules/gm) is very large, a small amount of water removes a significant amount of heat from the sample gas stream This cooling effect causes a significant temperature drop in the gas stream which can be measured by temperature measuring means 50. In this manner a very small amount of water can be used to achieve a significant temperature change with a known amount of heat energy (based upon the mass flow rate of the water) to allow determination of the absolute humidity in accordance with equations 1-3 above. It is important to note that this approach requires that a very fine atomization be achieved so that all water vapor metered into the system will be vaporized by the time the main fluid exits from outlet 24.

It will be appreciated that other means 16 for changing the heat energy of the sample stream may be used in lieu of injector tube 44. For example, the main gas stream can be heated or cooled by an electric resistance heater which is placed in the upstream end of mixing section 30 wherein the amount of heat energy (in watts) dissipated can be easily determined. By measuring the temperature difference between the incoming sample stream and the exiting stream of gas, the absolute humidity can easily be calculated utilizing equations 1 – 3 above. Similarly, a cooling coil, (for example a thermoelectric coil or a hollow coil carrying a circulated refrigerant) could easily be used to subtract a known amount of heat energy from the sample stream as it passes over the coils. This latter approach may be desirable where the gas stream is free of any type of particulates so that there is no problem of obstruction due to the collection of dirt, lint, or other debris.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. A device for measuring the absolute humidity in a sample stream of gas, said device comprising:
   - means for measuring the mass flow rate of said sample,
   - means for changing the heat energy per unit mass of said sample stream of gas by a predetermined amount;
   - means for measuring the temperature of said sample before the heat energy per unit mass of said sample is changed; and
   - means for measuring the temperature of said sample after the heat energy per unit mass of said sample is changed;
   - whereby said absolute humidity is determinable as a function of the measurements of (1) said mass flow rate, (2) said temperature of said sample before the heat energy per unit mass is changed, (3) said temperature of said sample after the heat energy per unit mass is changed, and (4) said predetermined amount of heat energy per unit mass of said sample stream.

2. A device in accordance with claim 1 wherein said means for measuring the mass flow rate of said sample includes a Venturi tube.

3. A device in accordance with claim 1, wherein said means for changing the heat energy per unit mass includes means for injecting a fluid into said stream.

4. A device in accordance with claim 3, wherein said means for injecting said fluid comprises a nozzle.

5. A device in accordance with claim 4 wherein said nozzle is a critical nozzle.

6. A device in accordance with claim 4 wherein said nozzle comprises a plurality of jets for injecting said fluid in a plurality of streams of fluid.

7. A device in accordance with claim 6 wherein said jets inject said streams of fluid transversely to said stream of gas to define a conical angle between said streams of between 90° and 180°.

8. A device in accordance with claim 4 wherein said means for changing the heat energy per unit mass further includes means for measuring the mass flow rate of said fluid injected by said nozzle.

9. A device in accordance with claim 8 wherein said means for measuring the mass flow rate of said fluid includes a critical nozzle and means for measuring the temperature of said fluid.

10. A device in accordance with claim 4 wherein said fluid is compressed air.

11. A device in accordance with claim 4 wherein said fluid is water.

12. A device in accordance with claim 1 wherein said means for changing the heat energy per unit mass includes a thermoelectric coil disposed in said sample stream.

13. A device in accordance with claim 1, wherein said means for changing the heat energy per unit mass includes a coil disposed in said sample wherein said coil contains a circulating refrigerant.

14. A device in accordance with claim 1 wherein both said means for measuring the temperature of said sample stream of gas include thermistors disposed within said sample stream.

15. A device in accordance with claim 14, wherein both said means for measuring said sample stream include thermocouples disposed within said sample stream.

16. A device in accordance with claim 1, wherein said means for changing the heat energy per unit mass includes an electrical resistance coil disposed in said sample stream.

17. A device in accordance with claim 1 wherein said absolute humidity is a function of the ratio of said predetermined amount of the change in heat energy per unit mass over the product of the measured mass flow rate of said sample times the difference between the measured temperature of said sample after said heat energy of said sample stream is changed and the measured temperature of said sample before said heat energy of said sample stream is changed.

18. A method of measuring the absolute humidity in a sample stream of gas, said method comprising the steps of:

measuring the mass flow rate of said sample,
changing the heat energy per unit mass of said sample stream of gas by a predetermined amount;
measuring the temperature of said sample before the heat energy per unit of said sample stream is changed;
measuring the temperature of said sample after the heat energy per unit mass of said sample is changed; and
determining said absolute humidity as a function of (1) said mass flow rate, (2) said temperatures of said sample before and after the heat energy per unit mass is changed, and (3) said predetermined amount of heat energy per unit mass.

19. A method in accordance with claim 18 wherein said step of changing the heat energy per unit mass of said sample includes the step of injecting a fluid into said stream.

20. A method in accordance with claim 19 wherein said step of changing the heat energy per unit mass further includes the step of measuring the mass flow rate of said fluid injected into said stream.

21. A method in accordance with claim 18, wherein said step of determining said absolute humidity includes determining the ratio of said predetermined amount of the change in heat energy per unit mass over the product of the measured mass flow rate of said sample times the difference between the measured temperature of the sample after the heat energy of said sample is changed and the measured temperature of said sample stream before the heat energy of said sample stream is changed.

* * * * *

UNITED STATES PATENT OFFICE
CERTIFICATE OF CORRECTION

PATENT NO. : 4,028,942
DATED : June 14, 1977
INVENTOR(S) : Frank J. Gardiner

It is certified that error appears in the above-identified patent and that said Letters Patent are hereby corrected as shown below:

Claim 18, column 10, line 2, after "unit" insert --mass--.

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*